United States Patent [19]

Deaton

[11] 4,148,869

[45] Apr. 10, 1979

[54] IMMUNOLOGICAL REAGENT AND METHOD OF USING SAME

[75] Inventor: Carlton D. Deaton, Garden Grove, Calif.

[73] Assignee: Baxter Travenol Laboratories, Inc., Deerfield, Ill.

[21] Appl. No.: 615,024

[22] Filed: Sep. 19, 1975

Related U.S. Application Data

[63] Continuation-in-part of Ser. No. 555,908, Mar. 6, 1975, abandoned.

[51] Int. Cl.$^2$ .................. G01N 21/00; G01N 23/00; G01N 31/00; B01D 21/01
[52] U.S. Cl. ..................... 424/1; 23/230 B; 195/103.5 A; 210/DIG. 23; 260/112 R; 260/112 B; 424/8; 424/11; 424/12; 424/13; 424/177
[58] Field of Search .............. 424/1, 8, 12, 177; 260/112 R, 112 B; 23/230 B, 253 TP; 210/DIG. 23; 195/103.5; 252/559

[56] References Cited

U.S. PATENT DOCUMENTS

| | | | |
|---|---|---|---|
| 3,489,688 | 1/1970 | Pospischil | 252/559 |
| 3,492,396 | 1/1970 | Dalton | 424/12 X |
| 3,624,197 | 11/1971 | Schain | 424/3 |
| 3,770,380 | 11/1973 | Smith | 424/12 X |
| 3,880,989 | 4/1975 | Garcia | 424/11 |
| 3,897,357 | 7/1975 | Carmello | 252/559 |

FOREIGN PATENT DOCUMENTS 48-32784   5/1973   Japan.

OTHER PUBLICATIONS

Savory, Clin. Chem, vol. 20, No. 8, 1974, pp. 1071–1075.
Tiffany, Clin. Chem., vol. 20, No. 8, 1974, pp. 1055–1061.
Lizana, Clin. Chem., vol. 20, No. 4, 1974, pp. 415–420.
Hellsing, Protides of Biol. Fluids, Pergamon Press, Gt. Britain, vol. 21, 1974, pp. 579–583.
Creighton, J of Immunology, vol. III, 1973, pp. 1219–1227.
Harrington, Immunochem., vol. 8, 1971, pp. 413–421.
Lundkvist, Immunology, vol. 23, 1972, pp. 413–422.

*Primary Examiner*—Anna P. Fagelson
*Attorney, Agent, or Firm*—Lawrence W. Flynn

[57] ABSTRACT

Immunological assaying methods which require insolubilization of an antigen-antibody complex as an integral step thereof are improved by adding to the test medium in which insolubilization is desired an aqueous reagent solution containing from about 3 to 6% by weight of a mixture of polyethylene glycol and a nonionic surfactant, and which solution has a calculated HLB (Hydrophilic-Lipophilic-Balance) of about 0.7 to 1.7. This solution increases the insolubilization of the antigen-antibody complex with reduced incubation times, and produces an assay procedure of greater test range and sensitivity. A preferred embodiment involves usage in a nephelometric analysis.

42 Claims, No Drawings

IMMUNOLOGICAL REAGENT AND METHOD OF USING SAME

CROSS REFERENCE TO RELATED APPLICATION

This is a continuation-in-part of application Ser. No. 555,908 filed March 6, 1975 now abandoned, in the name of the present inventor.

BACKGROUND OF THE INVENTION

This invention broadly relates to an immunological reagent solution which is useful for enhancing the extent of an immunoprecipitation reaction. More specifically, the invention relates to a reagent solution which can be utilized in a wide variety of immunological assaying methods which involve the reaction of an antigen and antibody to form an antigen-antibody complex, to substantially increase the extent of insolubilization of the antigen-antibody complex.

As generally appreciated by those skilled in the art, there are numerous immunological assaying methods of widely varying methodology which necessitate at one stage or another in the assay, and for varying purposes, the insolubilization of as much of the antigen-antibody complex as possible. For example, complex insolubilization plays an important role in such illustrative important conventional immunological assaying techniques as electrophoretic analysis, enzymatic assays, radioimmunoassays (RIA) and nephelometric assays, and much work has been directed toward developing means for increasing complex insolubilization in order to improve these assays. Normally, complex insolubilization is necessary in order to isolate the immunological reaction product from the unreacted immunological reactants involved in a particular assay so that either the isolated reaction product or the unreacted reactants can be separately analyzed to provide a meaningful diagnostic assay.

While the invention can be utilized in connection with a wide variety of immunological assaying methods, it is particularly useful in carrying out nephelometric analyses. Nephelometric, or light scattering, principles have been adapted to the determination of relatively small quantities of biological constituents which are made to exist in the form of suspended particles such as, for example, by the formation of an antigen-antibody complex. According to this method, a light source is made to pass through a liquid test sample whereby the light rays are directed through the suspended particles of the formed complex. As these light rays strike the particles, they are scattered or diffused at any predetermined angle, for example, at a right angle, from the axis of the bean and are received by photocells. This scattered light is converted to an electrical signal which is directly proportional to the amount of particulate concentration which, in turn, is thereby accurately measured on a meter face of an instrument.

The general principles of naphelometric immunological assays are well known. Examples of instruments suitable for nephelometric analyses are the Hyland Laser Nephelometer PDQ ™ (Hyland Laboratories); the Aminco-Fluorocolorimeter (American Instrument Company); the Aminco-Bowman Spectrophotofluorometer (SPF); and the Auto Analyzer II with attached Fluoronephelometer (Technicon Instruments Corporation).

By means of these nephelometric principles and equipment, the clinical technologist can make an accurate determination of small concentrations of a wide variety of specific proteins, for example, the immunoglobulins IgG, IgA, IgM, transferrin, complement C3, haptoglobin, alpha$_1$-antitrypsin, $\beta$-lipoprotein, albumin, alpha$_2$-macroglobulin, alpha$_1$-acid glycoprotein, and various other biological constituents such as triglycerides, lipoproteins, and human chorionic gonadotropins.

Since the test range and sensitivity of a nephelometric analysis in many cases depend in large part on the extent to which the antigen-antibody complex can be insolubilized, procedures have been developed recently for improving a nephelometric analysis in this respect by use of the polymer polyethylene glycol (PEG). See, for example, Hellsing, *Protides Biol. Fluids*, Proc. Colloq. 21, pp. 579–83 (1973); Lizane and Hellsing, Clin. Chem. 20, pp. 415–20 (1974); Savory et al., Clin. Chem. 20, pp. 1071–75 (1974); and Tiffany et al., Clin. Chem. 20, pp. 1055–61 (1974). According to these procedures, test samples are diluted with a solution of polyethylene glycol polymer prior to incubation of the sample and reading on the nephelometric instrument. The polyethylene glycol improves the nephelometric analysis by increasing the concentration of suspended particles, thereby improving the analysis. In effect, the polyethylene glycol is enhancing the insolubilization of the antigen-antibody complex. Despite this improvement, there remain many biological constituents which cannot be satisfactorily analyzed on a nephelometer because of inadequate test range of sensitivity caused by too low a concentration of suspended particles at the time the light scattering is performed.

It is therefore an object of this invention to provide an improved immunological reagent system which operates to greatly increase the insolubilization of antigen-antibody complexes beyond that obtainable from polyethylene glycol alone, and hence increase the concentration of suspended particles in a nephelometric analysis, and in various other immunological assaying methods which would benefit from improved insolubilization of the antigen-antibody complex.

It is another object of this invention to increase the test range and sensitivity of a nephelometric analysis and of other immunological assaying techniques which would benefit from improved insolubilization of the antigen-antibody complex.

These and other objects of this invention will be apparent to those skilled in the art from a consideration of this specification taken in its entirety.

SUMMARY OF THE INVENTION

The above objectives are accomplished by providing an immunological reagent for use in any of a variety of immunological assaying methods, which comprises at the time the reagent is used in the analysis an aqueous solution containing about 3 to 6% by weight of a mixture of polyethylene glycol and a nonionic surfactant other than polyethylene glycol, said solution further having a calculated HLB value of about 0.7 to 1.7 at the time it is used in the analysis. It has been surprisingly found that when the reagent of this invention is used in an immunological assaying method such as, for example, a nephelometric analysis, the extent of insolubilization of the antigen-antibody complex found during the assay is greatly increased over the use of polyethylene glycol alone. Moreover, incubation times are significantly reduced. The result is a greater concentration of insolubilized complex particles obtained at a shorter incubation time, and consequently improved test range and sensitivity. Similar observations apply to any immunological assaying methods which relies upon an antigen-antibody complex insolubilization step at some point during the assay procedure, for whatever the reason.

The HLB value is a well-established measure of the hydrophilic-lipophilic balance (hence "HLB") of a given surfactant. The HLB system of surfactant identification was developed by Atlas Chemical Industries, Inc. and is described in detail on pp. 28-36 of the Atlas publication entitled "Guide to the Use of Atlas Surfactants and Sorbitol in Cosmetic and Pharmaceutical Products" (1965), said publication incorporated herein by reference. Each surfactant is assigned an HLB number. The lower the HLB number, the more lipophilic (or oil-loving) the surfactant while the higher the number, the more hydrophilic (or water-loving) the surfactant. The method for establishing the HLB value of any given surfactant is well established, and is described in an Atlas publication entitled "The Atlas HLB System" (Code LD-97), available from Atlas on request. The HLB values of numerous surfactants are also published widely in the literature, particularly literature put out by the manufacturer of the surfactant in question.

The HLB value of a blend of surfactants, such as exist in the reagent of this invention, is a function of the concentration of each surfactant in the blend, and hence the concentration of the individual surfactants must be taken into account in computing an HLB value for the blend. The HLB value of the blend is calculated, in accordance with accepted published procedures, by multiplying the assigned HLB value of each surfactant present in the blend by its concentration in the composition in question, and adding the individual calculated results. For example, if the reagent of this invention contained 1% by weight polyethylene glycol (HLB=20) and 3% by weight of a nonionic surfactant having an HLB of 30.5, the HLB value of the reagent would be computed as follows:

| | | |
|---|---|---|
| 0.01 × 20 | = | 0.2 |
| | | + |
| 0.03 × 30.5 | = | 0.915 |
| | | 1.115 — HLB value of reagent |

To determine whether a given reagent has an HLB value which falls within the 0.7 to 1.7 range of the reagent of this invention a calculation as above, based on the amount of each component in the blend, can be readily made, using either published HLB values for the components in question or HLB values determined according to the Atlas method.

The present invention contemplates the use of a wide variety of nonionic surfactants in conjunction with the polyethylene glycol provided that (1) the mixture of nonionic surfactant and polyethylene glycol falls within a range of 3 to 6% by weight at the time the reagent is used in the assay, and (2) that the calculated HLB value of the reagent falls within a range of 0.7 to 1.7 at the same time. If at the time of use, the polyethylene glycol-nonionic surfactant mixture accounts for less than 3% of the reagent, or if the reagent has an HLB less than about 0.7, it becomes difficult to insolubilize the desired amount of antigen-antibody complex to the extent required for a successful completion of the immunological assay. On the other hand, if the mixture accounts for more than 6% of the reagent, or if the reagent has an HLB greater than about 1.7, other proteins besides the desired antigen-antibody complex are insolubilized, thereby destroying the selectivity of the assay and rendering the results meaningless.

Of course, the reagent solution could, for a variety of reasons, be prepared and marketed in such manner that it did not contain the requisite 3 to 6% mixture of polyethylene glycol and nonionic surfactant, or have the requisite HLB value of 0.7 to 1.7. Poor shelf stability could be one such reason. However, such solutions would require adjustment, prior to or at some point during their usage in an immunological assay technique, to the 3 to 6% range and to an HLB value of about 0.7 to 1.7. For this reason, reagents which do not contain the requisite 3 to 6% of said mixture or an HLB value of about 0.7 to 1.7, but which could be readily adjusted to these values prior to or during the immunological test procedure, are considered well within the scope of the invention, even though they fall outside the specific parameters of concentration and HLB range required during the assay procedure itself.

The marketed reagent solution, for example, may require dilution, concentration, or other adjustment steps prior to or at some convenient point during performance of the immunological assay method, for the purpose of bringing the solution to a mixture level of 3 to 6% and a calculated HLB value of 0.7 to 1.7. In such circumstances, the marketed solution would still fall within the scope of the present invention. Thus the reagent could be marketed at a mixture concentration higher than 6%, e.g., 8%, which would be diluted either prior to or at some suitable point during an immunological assay procedure to the 3 to 6% range. Similarly, the reagent could be marketed with a calculated HLB value outside the 0.7 to 1.7 range, but with the requirement that the reagent solution be in someway altered prior to or at some suitable point during an immunological assay procedure to bring it to a calculated HLB range of 0.7 to 1.7.

The reagent could in certain cases be diluted to the proper levels with the antiserum to be used in the test, while in other cases it could be diluted with the test sample or in some cases with both the test sample and antiserum. The important point is that at some point during the immunological assay procedure, usually either prior to or at the time of the antigen-antibody reaction, the requisite level of 3 to 6% of combined polyethylene glycol and nonionic surfactant, and the requisite HLB value of 0.7 to 1.7, must be provided in order for the reagent of the invention to function properly in the assay procedure. The point in the assay procedure at which these requisite parameters must be provided can vary depending on the particular procedure involved. For a nephelometric analysis, for example, it is convenient to prepare and market the reagent of the invention with a concentration of polyethylene glycol and nonionic surfactant in excess of 6% and at an HLB value outside the 0.7 to 1.7 range. Then, just prior to usage in the nephelometric analysis, the reagent is diluted with the antiserum to be used in the analysis to provide a concentration of polyethylene glycol and nonionic surfactant within the 3 to 6% range, and a calculated HLB value within the 0.7 to 1.7 range.

The invention finds utility in any immunological assaying method which would be benefited by enhanced insolubilization of the antigen-antibody complex at some point during the assay.

DESCRIPTION OF THE PREFERRED EMBODIMENTS

As previously discussed, the reagent solution contains about 3 to 6%, and preferably about 4%, of a mixture of polyethylene glycol and a nonionic surfactant. The relative proportions of polyethylene glycol and nonionic surfactant in the mixture can vary within wide limits, depending largely on the surfactant being used. Illustratively, the mixture contains from about 10 to 90% by weight polyethylene glycol and 10 to 90% nonionic surfactant. Preferably, the mixture contains about 15 to 85% polyethylene glycol and 15 to 85% nonionic surfactant.

One or more different forms or types of polyethylene glycol can be used as the polyethylene glycol component of the mixture. The polyethylene glycol polymer used generally has a molecular weight of from about 200 to about 10,000, and preferably from about 4,000 to about 6,000. These materials are available commercially, for example, from Union Carbide as CARBOWAX 4,000 or 6,000 and from Dow Chemical Company as PEG 4,000 or 6,000. A molecular weight range of about 4,000 is especially preferred.

The nonionic surfactant component of the mixture can be any nonionic surfactant which will produce in the reagent solution a calculated HLB value of 0.7 to 1.7, and preferably about 0.7 to 1.3, at a mixture concentration of 3 to 6%. Illustratively, the HLB values of the nonionic surfactant itself can range from about 10 to 30 or more.

A particularly preferred nonionic surfactant is a block copolymer of ethylene oxide and polyoxypropylene. This particular polymer and its preparation is described in U.S. Pat. No. 2,674,619. These block copolymers are generally prepared by condensing ethylene oxide with polyoxypropylene polymer and can be represented by the following structural formula:

$$HO(CH_2CH_2O)_a (CH_3CHCH_2O)_b (CH_2CH_2O)_c H.$$

For purposes of this invention these block copolymers desirably contain at least 50% ethylene oxide in the molecule and a polyoxypropylene hydrophobic base molecular weight of at least 950, similarly as described in U.S. Pat. Nos. 3,450,502, 3,577,522, and 3,590,125.

Illustrative examples of such suitable block copolymers are the F-38 and F-68 PLURONIC ® polyols sold by Wyandotte Chemicals Corporation. F-38 contains 80% of polyoxyethylene hydrophilic units in the molecule and the polyoxypropylene hydrophobic base has a molecular weight of 950. F-38 is a particularly preferred nonionic surfactant. F-68 also contains 80% of polyoxyethylene hydrophilic units in the molecule but the hydrophobic base has a molecular weight of 1,750. The total molecular weight of these two PLURONIC ® polyols is 4,750 and 8,750, respectively. PLURONIC ® L-125 has also been found useful. A further description of these polyols is found in the bulletin of Wyandotte Chemicals Corporation, "The Pluronic Grid" Sixth Edition, which is incorporated herein by reference.

In the case of PLURONIC nonionic surfactants, a mixture consisting of about 20% to 40% by weight polyethylene glycol and about 80% to 60% block copolymer of ethylene oxide and polyoxypropylene polymer is generally preferred.

A highly preferred reagent solution contains about one part by weight of polyethylene glycol having a molecular weight of about 4,000 and about three parts by weight of the Pluronic F-38 material. This solution can be prepared in a saline solvent (e.g., 0.9% NaCl) either at, above or below the desired level of 3 to 6% and then adjusted, if necessary, to the desired level of 3 to 6%. Preferably, the solution is prepared as an 8% solution of the polymer mixture in saline which is then diluted with antiserum (see Examples 1 and 5 below) or another suitable diluent prior to its usage in an immunological assay procedure. The diluted reagent thus contains about 1% polyethylene glycol and 3% F-38. Its HLB value of 1.115 can be calculated as follows:

| 1% PEG: | 0.01 × 20* | = | 0.2 |
|---|---|---|---|
| 3% F-38: | 0.03 × 30.5** | = | 0.915 |
| | | | 1.115 |

*the HLB of PEG from the literature is 20
**the HLB of F-38 from the literature is 30.5

Suitable assay results can also be achieved without the presence of the polyethylene glycol, for example, with an aqueous solution containing about 4% by weight of the block copolymer of ethylene oxide and polyoxypropylene. However, the mixture of block copolymer and polyethylene glycol described above is preferred.

A wide variety of other nonionic surfactants can also be used to complement the polyethylene glycol in the reagent solution of the invention, provided they provide the desired HLB value of 0.7 to 1.7 at a mixture concentration of 3 to 6%. For example, the TETRONIC ® series of nonionic surfactants available from BASF Wyandotte Corporation and described in detail in the BASF Wyandotte brochure entitled "Technical Data on Tetronic ® Series Nonionic Surfactants" and in U.S. Pat. No. 2,979,528 (said publication and patent incorporated herein by reference) have been found quite suitable, particularly those identified as TETRONIC ® 707, 908, 1107, 1307 and 1508. The TETRONIC ® products are based on ethylene diamine and have the general formula:

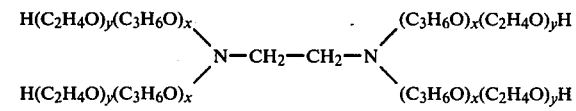

The molecular weight range of the TETRONIC ® line can vary from 1,650 to over 26,000. The more preferred TETRONIC ® surfactants have molecular weights in the range of about 15,000 to 27,000 and HLB values of about 20 to 30.5. The proportion of polyethylene glycol to TETRONIC ® surfactant in the mixture can vary widely, as discussed above.

Another family of useful nonionics is the PLURAFAC ® line of products also put out by BASF Wyandotte, particularly those identified as PLURAFAC ® 17R8, 25R8, D25, A38 and A39. The PLURAFAC ® products are straight chain, primary aliphatic oxyalkylated alcohols described in greater detail in the BASF Wyandotte brochure entitled "Technical Data on Typical Physical Properties of Plurafac ® Nonionic Surfactants". The preferred PLURAFAC ® products have HLB values of about 10 to 20 and can be used in widely varying ratios with the polyethylene glycol.

Another suitable nonionic surfactant is glycerol monostearate. A preferred glycerol monostearate is available from Atlas Industries, Inc. under the tradename ARLACEL 165 (HLB=11.0). The alkyl aryl sulfonates have also proven useful in the invention when combined with polyethylene glycol. A typical useful alkyl aryl sulfonate is also available from Atlas Industries, Inc. under the tradename G-3300 (HLB=11.7).

The above listing of nonionic surfactants is illustrative only since other such surfactants are contemplated to fall within the scope of the invention provided they provide a reagent which, when used in an immunological assay procedure, contains about 3 to 6% of a mixture of polyethylene glycol and surfactant, has a calculated HLB value based on the values of the individual components present in the solution of about 0.7 to 1.7, and produces the effect of enhancing the insolubilization of the desired antigen-antibody complex to the extent desired to improve the assay, and without insolubilizing unwanted components or in any other way detrimentally interfering with the assay procedure.

Of course, more than one nonionic surfactant can be present with the polyethylene glycol provided the requisite concentration of the mixture and HLB value of the solution are achieved.

In selecting a nonionic surfactant for use in the invention, one should be used which also has the capability of providing a clear reagent solution at least at the time the reagent solution is first used in the immunological assay procedure. This is to insure that the reagent does not interfere with the test results, or does not produce nonspecific precipitation of the components of the biological sample or the biological reagents employed in the assay system.

The reagent system of the invention finds broad utility as an improvement in a host of conventional immunological assay methods which at one time or another, for whatever the reason, require a step to insolubilize the antigen-antibody complex formed during the assay procedure by the antigen-antibody reaction. Such assay methods are well known to those skilled in the art and need not be repeated in detail herein. The applicability and usefulness of the present invention in these various assay methods, and the details of how to use the reagent of the invention in such procedures would be apparent to those skilled in the art from a reading of this specification and thus these specifics bear no exhaustive repeating herein. For example, the reagent of the invention could be used to enhance any system that depends upon the precipitation of antigen-antibody complexes to produce a clear supernatant fluid for fluorescence or colorimetric detection. The reagent could also be used to remove interfering substances found in biological fluids or reagents (e.g., lipids, salts, and extraneous proteins) for nephelometry, enzymatic or other assay systems. This is accomplished by the removal of the reactants from the reaction solution for the purpose of washing and resuspending these reactants.

Specifically, the reagent of the invention may be utilized to increase the relative concentration of insoluble antigen-antibody complexes and increase a given assay system's test range and sensitivity. These principles may be applied to quantitative light scattering from immune complexes by nephelometry, this being at present a preferred embodiment of the invention. Nephelometric analyses using the reagent of the invention are particularly useful in the analysis of various immunoglobulins. However, other test systems that are based on precipitating antibody may utilize these reagents, such as radioimmunodiffusion (RID), enzymatic analyses, and various types of electrophoretic techniques such as immunoelectrophoresis (IEP), counterelectrophoresis (CEP), and electroimmunodiffusion (EID).

The reagent of the invention may, for example, be used in enhancing immunological assays that depend upon the primary interaction of antigen-antibody coprecipitation technique commonly used in radioimmunoassays (RIA). This enhanced insolubilization characteristic of the present invention can also be utilized in the various methodologies of attachment of antibodies or antigen to inert particles used as a carrier in RIA, nephelometric, and fluorometric assays in a manner well understood by those skilled in the art.

Numerous radioimmunoassay techniques have been adopted to quantitate relatively small concentrations of biological constituents found in body fluids. Isotopically labeled antigen or antibody is reacted with the homologous antigen or antiserum to produce labeled immune antigen-antibody complexes. These complexes must then normally be rendered insoluble by an insoluble carrier, precipitating reagent or other known techniques. The free or non-reacted labeled antigen or antibody can be removed by washing techniques. The radioactive concentration of the precipitated complexes is then determined by gamma or liquid scintillation counting. An example of an instrument used for assays of this type is the Auto Gamma Counter (available from Nuclear Chicago, Inc.). The present reagent system is useful to enhance the requisite complex insolubilization step, thus improving the analysis. Example 6 below details the use of the reagent of the invention in a radioimmunoassay procedure.

Enzymatic techniques have also been adopted to quantitate small concentrations of biological constituents found in body fluids. Enzyme labeled antigen or antibody is reacted with the specific antibody or antigen to produce immune labeled antigen-antibody complexes. These complexes are rendered insoluble by an insoluble carrier, precipitating reagent or other technique. The free or non-reacted enzyme-labeled antibody or antigen may be removed by washing techniques. The bound or reacted enzyme can then produce a reaction with an appropriate substrate to produce a colored or fluorescent supernatant solution which can be measured with a spectrophotometer or fluorometer. Examples of instruments useful for this purpose are the Beckman DB Spectrophotometer (available from Beckman Instruments, Inc.) and the Aminco-Bowman Spectro-photo-fluorometer (available from the American Instrument Company). The present reagent system is useful to enhance the requisite complex insolubilization step, thus improving the analysis.

The usefulness of the reagent in a nephelometric analysis has been discussed in detail above, and is further exemplified in Example 5 below.

It is now clear to those skilled in the art that the improved immunological reagent of the invention has wide ranging utility in the field of immunological assay procedures. Using the improved reagent, the clinical technologist can make accurate determination of a broad range of concentrations of many specific proteins, for example, the immunoglobulins IgG, IgA, IgM, transferrin, complement C3, haptoglobin, alpha$_1$-antitrypsin, $\beta$-lipoprotein, albumin, alpha$_2$-macroglobulin, alpha$_1$-acid glycoprotein, and various other biological constituents such as triiodothyonine (T$_3$), thyroxine (T$_4$), triglycerides, human chorionic gonadotropins, lipoproteins, and many others whose determination would benefit from the enhanced insolubilization effect produced by the present invention.

In most of the applications in which the invention finds utility, the desired test biological constituent or constituents are admixed with the aqueous reagent solution of the invention, incubated for a predetermined period of time such as, for example, at room temperature (20°–25° C.) for approximately one hour, and then read on appropriate instrumentation, e.g., a nephelometer in the case of a nephelometric analysis. The results of the test samples are compared with reference samples to determine the unknown concentration.

The following examples are intended to further illustrate the invention, although it will be understood that the invention is not limited to these specific examples.

EXAMPLE 1

A reagent solution is prepared by admixing 25 parts by weight of polyethylene glycol having a molecular weight of 4,000 with 75 parts by weight of PLURONIC F-38, and the mixture dissolved in normal saline (0.9% NaCl) to a concentration of 8% by weight of said mixture. This solution may optionally be diluted, such as with antiserum, to a mixture concentration of 4% (HLB ratio–1.115) as in step 3 of Example 5 below, prior to incubation, and used directly in an immunological assay procedure, or it can be kept in the 8% form until ready for use.

EXAMPLE 2

Example 1 is repeated, except that polyethylene glycol having a molecular weight of 6,000 is substituted for an equivalent amount of 4,000 material.

EXAMPLE 3

Example 1 is repeated except that PLURONIC F-68 is substituted for an equivalent amount of F-38.

EXAMPLE 4

Example 1 is repeated except that Tetronic 707, 908, 1107, 1307, 1508; Plurafac 17R8, 25R8, D25, A38 and A39; Pluronic L125; Arlacel 165; and G-3000 were substituted for the F-38 in varying amounts in a series of experiments to prepare a wide variety of reagent solutions.

EXAMPLE 5

The immunological reagent solutions prepared in Examples 1–4 are used in separate nephelometric assays of immunoglobulins (IgA, IgG, IgM), complement C3 and transferrin, with each assay being conducted as follows:
1. Reference controls No. 1, No. 2, No. 3, No. 4, No. 5, No. 6 (of known assay) for each said biological constituent are diluted 1:100 in saline.
2. The unknowns are then similarly diluted 1:100 in saline.
3. Prediluted antiserums to IgG, IgM, IgA, C3 and transferring are each diluted 1:2 with the 8% mixture of the immunological reagent from Examples 1, 2, 3, or 4 (as the case may be) and mixed by inversion to produce a 4% concentration of the polyethylene glycol and nonionic surfactant in the solution and a calculated HLB of between 0.7 and 1.7 in all cases.
4. The antiserum is filtered through a 0.45 μ Millipore filter.
5. A series of test tubes (10 mm × 75 mm disposable culture tubes) appropriately labeled blank, reference controls No. 1, No. 2, No. 3, No. 4, No. 5, No. 6, and unknown, are prepared.
6. To each tube, 1 ml of the diluted mixture of antiserum and reagent prepared in step 3 is added.
7. To the appropriate tube 25 μl of reference and unknown dilutions are added for IgG, IgA, and transferrin (100 μl for IgM and C3).
8. The appropriate blank tube correspondingly received 25 or 100 μl of saline.
9. The tubes are mixed by inversion and incubated for 1 hour at room temperature (20°–25° C.).
10. Sample blanks are prepared by using 1 ml of the filtered reagents from Examples 1–4, (as the case may be) prepared as in step 3 except that the 8% solution was diluted with saline instead of antiserum. The blanks are placed in identical labeled tubes as before (steps 5 and 6).
11. The same reference and sample volumes are added to each tube as before (step 7).
12. All tubes are read in the Laser Nephelometer PDQ ™ (Hyland Laboratories) for relative percent light scatter.
13. The blanks are read and subtracted electronically from the reaction values by the instrument.
14. The reference results are plotted on linear graph paper as relative percent light scatter versus concentration of references.
15. The unknown values are determined by reading from the reference curve.

The immunological reagents of the invention used in this sample produced substantially greater precipitation of the antigen-antibody complexes, more linearity over a wider range, and greater sensitivity than was obtained from a reagent containing polyethylene glycol alone.

EXAMPLE 6

This example describes the use of the immunological reagent of the invention in a radioimmunoassay procedure for the determination of human thyroid stimulating hormone (HTSH).

A sample of the immunological reagent of the invention was prepared by mixing 8.4 ml of a 5% solution of polyethylene glycol in 0.9 saline solution with 20 ml of 6% Pluronic F-38 nonionic surfactant. The volume of the mixture was then adjusted to 30 ml with 0.9 saline solution to give a final reagent concentration of 1.4% polyethylene glycol and 4.2% F-38.

The radioimmunoassay was performed as follows: 0.050 ml of Rabbit anti-HTSH absorbed with human chorionic gonadotropin (HCG) was mixed with 0.200 ml of HTSH standards of varying strength. 0.050 ml of a phosphate buffer, pH 7.4, was then added to the mixture and the mixture incubated for 2 hours at 37° C. At this point, 0.100 ml of HTSH tagged with I$^{125}$ was added and the mixture further incubated for 3 hours at 37° C. 1.0 ml of the reagent of the invention prepared above was then added and the mixture incubated for one hour at room temperature. Due to dilution of the reagent upon addition to the mixture, the concentration of polyethylene glycol and F-38 was reduced from 1.4 to 4.2% to 1 and 3% by weight respectively. The mixture was centrifuged at 1000×9 for 10 minutes. If a wash of the centrifuged solids is required, the wash solution must contain the same concentration as the reagent of the invention at the time the reagent was first used in the assay, i.e., 1% polyethylene glycol and 3% F-38. The supernatant liquid was then decanted and the precipitate counted. This procedure was repeated for a variety of differing HTSH standards and a standard curve was obtained by plotting the counts in the various precipitates versus the concentration of corresponding HTSH standard.

Once the standard curve had been obtained the assay was then performed on unknown test samples, using the procedure described above, except that the HTSH standard was replaced by the test sample. The HTSH level in the test sample could then be readily determined from the location of the precipitate count on the standard curve.

The use of the reagent solution of the invention enhanced the extent of precipitate which was formed beyond that obtainable from a reagent using polyethylene glycol alone, and resulted in an improved radioimmunoassay.

The above examples and other specific information contained herein are for purposes of illustration only, and such alterations and modifications thereof as would be apparent to those skilled, in the art, are deemed to fall within the scope and spirit of the invention, bearing in mind that the invention is defined only by the claims appended hereto.

What is claimed is:

1. A reagent for clinical nephelometric analysis comprising an aqueous solution of an antiserum to the component to be assayed and a mixture of about 20% to about 40% by weight polyethylene glycol having a molecular weight of about 200 to about 10,000 and about 80% to about 60% by weight of a block copolymer of ethylene oxide and polyoxypropylene containing at least 50% ethylene oxide.

2. The reagent of claim 1 in which the concentration of said mixture is about 4% by weight, and wherein said mixture contains about 25% by weight polyethylene glycol and about 75% by weight of said block copolymer.

3. The reagent of claim 1 in which the concentration of said mixture is from about 3% to about 6% by weight.

4. The reagent of claim 3 wherein the polyethylene glycol has a molecular weight of about 4,000 to 6,000.

5. In an immunological assaying method which involves a reaction between an antigen and an antibody to form an antigen-antibody complex, the improvement which comprises carrying out said reaction in the presence of a reagent comprising an aqueous solution containing about 3 to 6% by weight of a mixture of polyethylene glycol having a molecular weight of about 200 to about 10,000 and a nonionic surfactant other than polyethylene glycol wherein said mixture contains about 10% to 90% by weight polyethylene glycol and about 10% to 90% by weight nonionic surfactant and said solution has a calculated HLB value of about 0.7 to 1.7.

6. The method of claim 5 wherein said reagent is utilized in a nephelometric analysis.

7. The method of claim 5 wherein said reagent is utilized in a radioimmunoassay.

8. The method of claim 5 wherein said reagent is utilized in an enzymatic assay.

9. The method of claim 5 wherein said reagent is utilized in an electrophoretic assay.

10. The method of claim 5 wherein the polyethylene glycol has a molecular weight of about 4,000 to 6,000.

11. In a nephelometric immunoassay of a biological constituent which involves a reaction between said constituent with its antibody, the improvement comprising incubating said constituent, prior to conducting the light scattering measurements, in a reagent comprising an aqueous solution containing about 3 to 6% by weight of a mixture of polyethylene glycol having a molecular weight of about 200 to about 10,000 and a nonionic surfactant other than polyethylene glycol wherein said mixture contains about 10% to 90% by weight polyethylene glycol and about 10% to 90% by weight nonionic surfactant and said solution has a calculated HLB value of about 0.7 to 1.7.

12. The method of claim 11 wherein the polyethylene glycol has a molecular weight of about 4,000 to 6,000.

13. The method of claim 11 wherein the polyethylene glycol has a molecular weight of about 4,000 to 6,000 and said mixture contains about 15% to 85% polyethylene glycol and about 15% to 85% nonionic surfactant.

14. In a nephelometric immunoassay of a biological constituent, the improvement comprising incubating said constituent, prior to conducting the light scattering measurements, in a reagent comprising an aqueous solution containing an antiserum to said constituent and about 3 to 6% by weight of a mixture of polyethylene glycol having a molecular weight of about 200 to about 10,000 and a nonionic surfactant other than polyethylene glycol wherein said mixture contains about 10% to 90% by weight polyethylene glycol and about 10% to 90% by weight nonionic surfactant and said solution has a calculated HLB value of about 0.7 to 1.7.

15. The method of claim 14 wherein the polyethylene glycol has a molecular weight of about 4,000 to 6,000.

16. In a nephelometric analysis of an immunoglobulin which involves a reaction between said immunoglobulin with its antibody, the improvement comprising incubating said immunoglobulin, prior to conducting the light scattering measurements, in a reagent comprising an aqueous solution containing about 3 to 6% by weight of a mixture of about 20% to about 40% by weight polyethylene glycol having a molecular weight of about 200 to about 10,000 and about 80 to about 60% by weight of a block copolymer of ethylene oxide and polyoxypropylene.

17. The method of claim 16 wherein the polyethylene glycol has a molecular weight of about 4,000 to 6,000.

18. In an immunological assaying method which involves a reaction between an antigen and an antibody to form an antigen-antibody complex, the improvement which comprises carrying out said reaction in the presence of a reagent comprising an aqueous solution containing about 3 to 6% by weight of a mixture of polyethylene glycol having a molecular weight of about 200 to about 10,000 and a nonionic surfactant selected from the group consisting of:
   (a) a block copolymer of ethylene oxide and polyoxypropylene,
   (b) straight chain primary aliphatic oxyalkylated alcohols, and
   (c) glycerol monostearate, wherein said mixture contains about 10% to 90% by weight polyethylene glycol and about 10% to 90% by weight nonionic surfactant and said solution has a calculated HLB value of about 0.7 to 1.7.

19. The method of claim 18 wherein the polyethylene glycol has a molecular weight of about 4,000 to 6,000.

20. A reagent for use in an immunological assay comprising an aqueous solution containing a mixture of (1) polyethylene glycol having a molecular weight of about 4,000 to about 6,000, (2) a block copolymer of ethylene and polyoxypropylene and (3) an antiserum to the component to be assayed, wherein the combined amount of polyethylene glycol and block copolymer present in the solution is about 3 to 6% by weight and comprises about 20% to about 40% by weight polyethylene glycol and about 80% to about 60% by weight block copolymer, and wherein the calculated HLB value of the solution is about 0.7 to 1.7.

21. The reagent of claim 20 wherein the antiserum is an antiserum to a member selected from the group consisting of IgG, IgM, IgA, complement C3 and transferrin.

22. A reagent for use in an immunoassay comprising an aqueous solution containing about 3 to 6% by weight of a mixture of polyethylene glycol having a molecular weight of about 200 to about 10,000 and a nonionic surfactant other than polyethylene glycol, said mixture containing about 10 to 90% by weight polyethylene glycol and about 10 to 90% by weight nonionic surfactant, and wherein said solution has a calculated HLB value of about 0.7 to 1.7 provided, however, that when the nonionic surfactant is a block copolymer of ethylene oxide and polyoxypropylene the block copolymer contains at least 50% ethylene oxide.

23. The reagent of claim 22 wherein the polyethylene glycol has a molecular weight of about 4,000 to 6,000.

24. In a nephelometric immunoassay of a biological constituent wherein said biological constituent undergoes an immunoreaction, the improvement comprising diluting an aqueous solution containing polyethylene glycol having a molecular weight of about 200 to about 10,000 and a nonionic surfactant other than polyethylene glycol to produce a diluted solution containing about 3 to 6% by weight of a mixture of polyethylene glycol and said nonionic surfactant having a calculated HLB value of about 0.7 to 1.7, said mixture containing about 10–90% by weight polyethylene glycol and about 10–90% by weight nonionic surfactant, and contacting said biological constituent with said diluted solution either prior to or at the time of said immunoreaction and prior to conducting the light scattering measurements.

25. The immunoassay of claim 24 wherein the polyethylene glycol has a molecular weight of about 4,000 to 6,000.

26. The method of claim 24 wherein the biological constituent is selected from the group consisting of IgG, IgA, IgM, transferrin, complement C3, haptoglobin, alpha$_1$-antitrypsin, albumin, alpha$_2$-macroglobulin, alpha$_1$-acid glycoprotein, T-3, T-4, triglycerides, human chorionic ganodotropins and lipoproteins.

27. The immunoassay of claim 24 wherein the polyethylene glycol has a molecular weight of about 4,000 to 6,000 and said mixture contains about 15% to 85% polyethylene glycol and about 15% to 85% nonionic surfactant.

28. The immunoassay of claim 27 wherein the nonionic surfactant is a block copolymer of ethylene oxide and polyoxypropylene.

29. In a nephelometric immunoassay of a biological constituent, the improvement comprising diluting with an antiserum for said biological constituent an aqueous solution containing polyethylene glycol having a molecular weight of about 200 to about 10,000 and a nonionic surfactant other than polyethylene glycol to produce a diluted solution containing about 3 to 6% by weight of a mixture of polyethylene glycol and said nonionic surfactant wherein said mixture contains about 10% to 90% by weight polyethylene glycol and about 10% to 90% by weight nonionic surfactant and said solution has a calculated HLB value of about 0.7 to 1.7, and contacting said biological constituent with said diluted solution prior to conducting the light scattering measurements.

30. The method of claim 29 wherein the biological constituent is selected from the group consisting of IgG, IgA, IgM, transferrin, complement C3, haptoglobin, alpha$_1$-antitrypsin, albumin, alpha$_2$-macroglobulin, alpha$_1$-acid glycoprotein, T-3, T-4, triglycerides, human chorionic ganadotropins and lipoproteins.

31. The immunoassay of claim 29 wherein the polyethylene glycol has a molecular weight of about 4,000 to 6,000.

32. The immunoassay of claim 41 wherein the antiserum is a prediluted antiserum.

33. The immunoassay of claim 32 wherein the polyethylene glycol has a molecular weight of about 4,000 to 6,000.

34. In an immunoassay which produces an antigen-antibody complex, the improvement comprising diluting with an antiserum for said antigen or antibody an aqueous solution containing polyethylene glycol having a molecular weight of about 200 to about 10,000 and a nonionic surfactant other than polyethylene glycol to produce a diluted solution containing about 3% to 6% by weight of a mixture of polyethylene glycol and said nonionic surfactant wherein said mixture contains about 10% to 90% by weight polyethylene glycol and about 10% to 90% by weight nonionic surfactant and said solution has a calculated HLB value of about 0.7 to 1.7, and producing the antigen-antibody complex in the presence of said diluted solution.

35. The method of claim 34 wherein the biological component is selected from the group consisting of IgG, IgA, IgM, transferrin, complement C3, haptoglobin, alpha$_1$-antitrypsin, albumin, alpha$_2$-macroglobulin, alpha$_1$-acid glycoprotein, T-3, T-4, triglycerides, human chorionic ganadotropins and lipoproteins.

36. The method of claim 34 wherein the nonionic surfactant is a block copolymer of ethylene oxide and polyoxypropylene, the calculated HLB value of the diluted solution is about 0.7 to 1.3, and the biological component is selected from the group consisting of IgG, IgA, IgM, complement C3, transferrin, T3 and T4.

37. The immunoassay of claim 34 wherein the polyethylene glycol has a molecular weight of about 4,000 to 6,000.

38. The immunoassay of claim 34 wherein the antiserum is a prediluted antiserum.

39. The immunoassay of claim 38 wherein the polyethylene glycol has a molecular weight of about 4,000 to 6,000.

40. In an immunological assaying method which involves a reaction between an antigen and an antibody to form an antigen-antibody complex, the improvement which comprises carrying out said reaction in the presence of a reagent comprising an aqueous solution containing about 3% to 6% of a mixture of polyethylene glycol having a molecular weight of about 200 to about 10,000 and an alkyl aryl sulfonate wherein said mixture contains about 10% to 90% by weight polyethylene glycol and about 10% to 90% by weight alkyl aryl sulfonate and said solution has a calculated HLB value of about 0.7 to 1.7.

41. The method of claim 40 wherein the immunological assaying method is a nephelometric analysis.

42. The method of claim 40 wherein the polyethylene glycol has a molecular weight of about 4,000 to 6,000.

* * * * *

UNITED STATES PATENT AND TRADEMARK OFFICE
CERTIFICATE OF CORRECTION

PATENT NO. : 4,148,869
DATED : April 10, 1979
INVENTOR(S) : Carlton D. Deaton

It is certified that error appears in the above-identified patent and that said Letters Patent are hereby corrected as shown below:

In column 14, line 16, "41" should read --29--.

Signed and Sealed this

Sixteenth Day of October 1979

[SEAL]

Attest:

RUTH C. MASON
Attesting Officer

LUTRELLE F. PARKER
Acting Commissioner of Patents and Trademarks